United States Patent [19]

Henry et al.

[11] Patent Number: 4,906,800
[45] Date of Patent: Mar. 6, 1990

[54] PROCEDURE FOR IMPARTING SELECTIVITY TO HYDROGENATION CATALYSTS AND METHOD FOR USING THE SAME

[75] Inventors: JoAnn Henry, Bedford Heights; Michael J. Desmond, Cleveland Heights, both of Ohio; Thomas R. Gaffney, Allentown, Pa.

[73] Assignee: The Standard Oil Company, Cleveland, Ohio

[21] Appl. No.: 901,663

[22] Filed: Nov. 17, 1986

[51] Int. Cl.$^4$ .............................................. C07C 5/09
[52] U.S. Cl. .................................. 585/260; 585/261; 585/322; 585/329
[58] Field of Search ............... 585/322, 329, 259, 260, 585/261, 262

[56] References Cited

U.S. PATENT DOCUMENTS

| | | |
|---|---|---|
| 3,308,180 | 3/1967 | Flemming . |
| 3,325,556 | 6/1987 | De Rosset . |
| 3,555,106 | 1/1971 | Ohmori ................................. 585/262 |
| 4,211,640 | 7/1980 | Garwood et al. ................... 208/255 |
| 4,227,992 | 10/1980 | Garwood et al. ..................... 208/46 |
| 4,230,897 | 10/1980 | Cosyns et al. ........................ 585/260 |
| 4,260,839 | 4/1981 | Chen et al. ............................ 585/257 |
| 4,387,258 | 6/1983 | Vadekar et al. ..................... 585/259 |
| 4,450,311 | 5/1984 | Wright et al. ......................... 585/413 |
| 4,456,779 | 6/1984 | Owen et al. .......................... 585/415 |
| 4,511,747 | 4/1985 | Wright et al. ......................... 585/415 |
| 4,533,779 | 8/1985 | Boitiaux et al. ...................... 585/260 |

FOREIGN PATENT DOCUMENTS

| | | | |
|---|---|---|---|
| 1004609 | 9/1965 | United Kingdom | ................ 585/262 |
| 1049145 | 11/1966 | United Kingdom | ................ 585/262 |
| 1133253 | 11/1968 | United Kingdom | ................ 585/260 |
| 1161645 | 8/1969 | United Kingdom | ................ 585/261 |
| 85302916 | 4/1985 | World Int. Prop. O. . | |

OTHER PUBLICATIONS

PCT/US85/00770 (Nov., 1985) Mazurek et al.
W. L. Kranich et al., *Applied Catalysis*, 13 (1985) pp. 257–267.

*Primary Examiner*—Asok Pal
*Attorney, Agent, or Firm*—Larry W. Evans; Joseph G. Curatolo; Sue E. Phillips

[57] ABSTRACT

This invention relates to a method for the preparation of selective acetylene hydrogenation catalysts. More specifically, this invention relates to a pretreatment method for supported and unsupported Group VIII metal catalysts and the use thereof for the conversion of an acetylene-, ethylene- and hydrogen-containing feedstream to gasoline range hydrocarbons.

45 Claims, 2 Drawing Sheets

% CONVERSION AND % SELECTIVITY VS. TEMPERATURE FOR $C_2H_2$ TO $C_2H_4$ OVER Pd-Pb/$CaCO_3$, $H_2/C_2H_2 \sim 1.0$ % CONVERSION AND % SELECTIVITY VS. TEMPERATURE FOR $C_2H_2$ TO $C_2H_4$ OVER $Pd-Pb/CaCO_3$, $H_2/C_2H_2 \sim 10.0$

PROCEDURE FOR IMPARTING SELECTIVITY TO HYDROGENATION CATALYSTS AND METHOD FOR USING THE SAME

FIELD OF THE INVENTION

This invention relates to a method for the preparation of selective acetylene hydrogenation catalysts. More specifically, this invention relates to a pretreatment method for supported and unsupported Group VIII metal catalysts and the use thereof for the conversion of an acetylene-, ethylene- and hydrogen-containing feedstream to gasoline range hydrocarbons.

BACKGROUND OF THE INVENTION

Hydrogenation catalysts can be used to hydrogenate the acetylene content of a given feedstream to ethylene. An acidic zeolite catalyst can then be used to convert ethylene to useful and commercially viable gasoline range hydrocarbons, or $C_5+$ liquid products. The original feedstream often, however, contains excess hydrogen and ethylene which hinder the selective conversion of acetylene to ethylene, instead converting the feedstream to ethane. A hydrogenation catalyst which operates efficiently in the presence of excess ethylene and hydrogen, eliminating the problem of feedstream conversion to ethane, would be advantageous.

The hydrogenation of acetylene to ethylene is a known process for the removal of small amounts of acetylene from ethylene feedstocks. Typically, highly dispersed palladium on a medium surface area support is used. Hydrogen is either added in stoichiometric amounts or in a slight molar excess and the gas is treated until complete hydrogenation of acetylene occurs. The feedstock, however, often contains both acetylene and ethylene, therefore requiring that the catalyst be selective for the hydrogenation of acetylene to ethylene over the hydrogenation of ethylene to ethane. Stoichiometric hydrogen to acetylene ratios are often used in conjunction with acetylene selective catalysts to ensure that feed ethylene is not hydrogenated to ethane, as well as that the ethylene produced from acetylene hydrogenation is not further hydrogenated to ethane. Catalysts which are selective in the presence of excess hydrogen have been documented. Most often, however, the selectivity of these catalysts is achieved by intentionally poisoning the catalysts with a variety of substances which impart selectivity. The poison is added to the feed gas in low concentration and must be present throughout the reaction in order for high selectivity to be maintained.

U.S. Pat. No. 3,308,180 discloses a process for the separation of acetylene from a feedstream containing both acetylene and ethylene by selective hydrogenation with a catalyst containing 0.01 to 0.1 wt % palladium on an alumina support.

U.S. Pat. No. 3,325,556 discloses a process for the selective hydrogenation of acetylene in an acetylene-/ethylene-containing mixture by the addition of carbon monoxide to this mixture and treatment thereof with an excess of hydrogen at elevated temperature and pressure in the presence of a catalyst comprising a noble metal disposed on alumina.

Palladium zeolite catalysts used to selectively hydrogenate acetylene in the presence of ethylene were reported by W. L. Kranich et al., Applied Catalysis, 13 (1985), 257–267.

U.S. Pat. No. 4,387,258 relates to the selective hydrogenation of unsaturated hydrocarbon feeds using catalysts comprising a catalytically-active metal on a crystalline silica support.

Catalysts of the zeolite variety used for treatment of olefinic gasoline are disclosed in U.S. Pat. Nos. 4,211,922; 4,277,992; 4,260,839; 4,450,311; 4,456,779; and 4,511,747.

International Application PCT/US85/00770 discloses a catalyst system useful for converting an ethylene-containing feedstock to heavier hydrocarbons in the gasoline or distillate boiling range. The system involves passing the feedstock over a siliceous crystalline molecular sieve to convert ethylene to $C_3$–$C_4$ olefins and $C_5+$ hydrocarbons, separating the olefins and $C_5+$ hydrocarbons, and then passing the olefins over a second siliceous molecular sieve to obtain heavier hydrocarbons.

What is lacking in the art, however, is a hydrogenation catalyst operative for the conversion of acetylene to ethylene, from a feedstream containing a relatively high ratio of acetylene to ethylene, such as 0.1 or greater, in the presence of ethylene and excess hydrogen. Also lacking is a single-pass conversion process using such a hydrogenation catalyst in conjunction with an acidic zeolite catalyst for the conversion of an acetylene-, ethylene- and hydrogen-containing feedstream to gasoline range hydrocarbons.

It is an object of the present invention, therefore, to develop a process for treating an acetylene hydrogenation catalyst to impart greater selectivity for acetylene to ethylene conversion to the catalyst when used in the presence of ethylene and excess hydrogen.

It is a further object of the present invention to provide a single-pass process which uses the pretreated hydrogenation catalyst in conjunction with an acidic zeolite catalyst to convert an acetylene-, ethylene- and hydrogen-containing feedstream to gasoline range hydrocarbons.

Other objects, aspects and advantages of the present invention will be apparent to those skilled in the art upon consideration of the following description of this invention and of the appended claims.

SUMMARY OF THE INVENTION

The present invention relates to a pretreatment method for imparting increased selectivity to acetylene hydrogenation catalysts comprising at least one cycle comprising the steps of:

(a) oxidizing the catalyst;

(b) reducing the catalyst in the presence of carbon monoxide and hydrogen;

(c) reducing the catalyst in the presence of hydrogen; and (d) thermolyzing the reduced catalyst, wherein the catalyst is purged under a flow of inert gas between each step.

The invention further relates to a method for the selective conversion of an acetylene-, ethylene- and hydrogen-containing feedstream to gasoline range hydrocarbons comprising the steps of:

(a) converting the acetylene component of the feedstream to ethylene by passing the feedstream first over an acetylene hydrogenation catalyst prepared by the treatment method as recited above; and (b) converting the ethylene-containing product from step one above to gasoline range hydrocarbons by passing the ethylene over a catalyst system suitable for such conversion.

DESCRIPTION OF THE PREFERRED EMBODIMENTS

Figure 1:
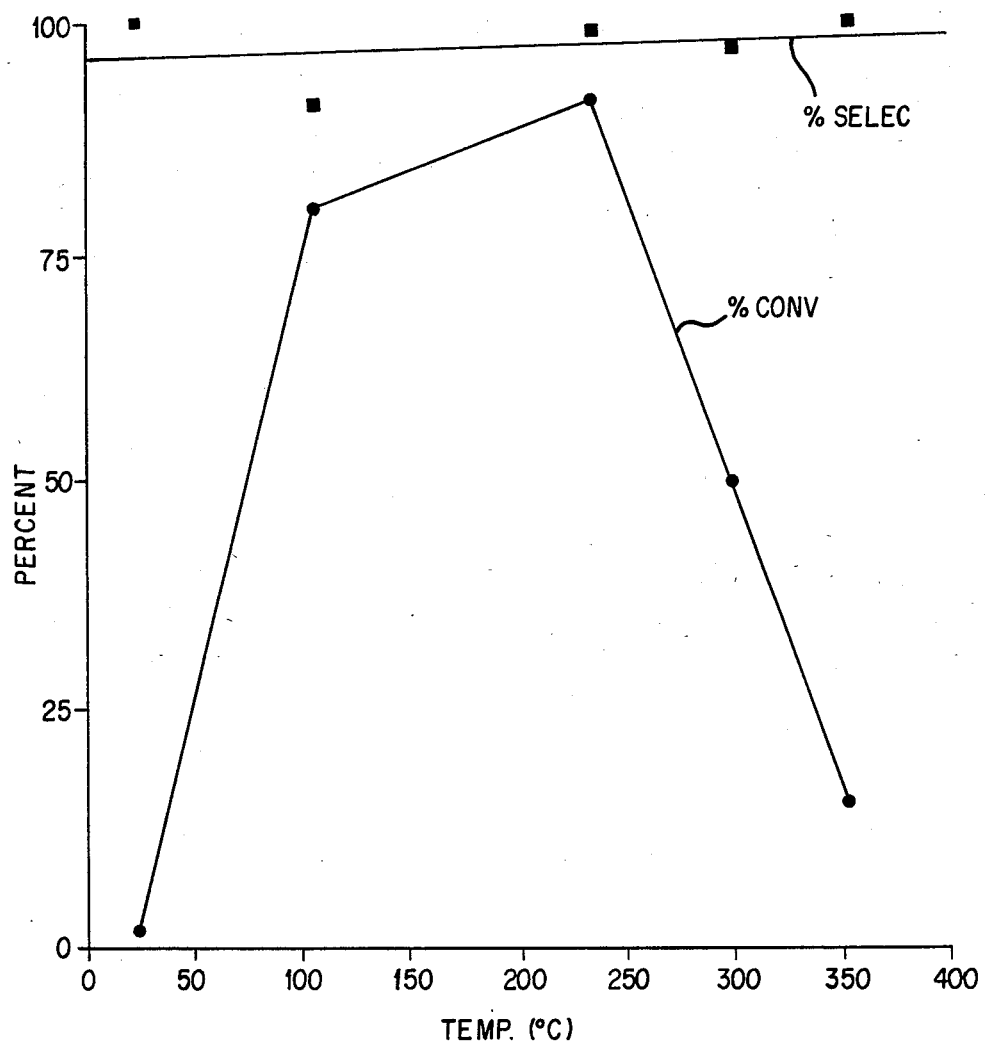
FIG. 1 is a plot of conversion and selectivity results of a run of synthetic pyrolysis effluent gas (PEG) passed over an untreated catalyst at temperatures from 25°–350° C.

In accordance with this invention there is provided a novel method for the pretreatment of acetylene hydrogenation catalysts for imparting increased selectivity to the catalysts. The catalysts thus treated can then be utilized for the conversion of an acetylene-, ethylene- and hydrogen-containing feedstream to gasoline range hydrocarbons. An examplary gas feedstream, which was used in the preferred embodiment of this invention, is pyrolysis effluent gas (PEG), which as used herein refers to the effluent gas from natural gas pyrolysis. PEG generally contains unsaturated hydrocarbons, such as acetylene and ethylene, in addition to hydrogen or unreacted paraffins, such as methane. The term "gasoline range hydrocarbons" as used herein refers to the $C_5+$ liquid products resulting from the ethylene conversion step of the subject invention. The terms "thermolysis" and "thermolyzing" as used herein refer to the heating of the catalyst in an inert atmosphere.

According to the preferred embodiment of the subject invention, acetylene from a PEG feedstream which contains ethylene and excess hydrogen is hydrogenated to ethylene. The approximate composition of the PEG used in the Examples below was about 2% ethylene, about 2% acetylene, about 10% carbon dixoide, about 30% hydrogen and about 56% methane. The subject catalyst is operable, however, for any acetylene-containing feedstream having more than stoichiometric amounts of hydrogen and acetylene. A hydrogenation catalyst operable in ethylene and excess hydrogen, and yet selective for the conversion of acetylene to ethylene over the conversion of ethylene to ethane, is therefore necessary to convert such a feedstream to a form suitable for further conversion to gasoline range hydrocarbons.

Hydrogenation catalysts useful in the inventive method herein disclosed consist of supported and unsupported Group VIII metals. Examples of this type of catalyst include but are not limited to Raney nickel, palladium supported on barium sulfate and palladium supported on carbon, as well as other related nickel, platinum, cobalt, rhodium, iridium, iron and ruthenium based catalysts. Often, promoters, such as lead, tin, bismuth, and antimony, or basic compounds containing nitrogen, phosphorus, sulfur and arsenic, such as pyridine, tributylamine and diphenyl sulfide, are added in incremental amounts. Such catalysts are effective for treating feed mixtures that contain high concentrations of acetylene.

An example of such a catalyst would be about 5wt. % Pd on a $CaCO_3$ support containing about 35% Ca, and about 3% Pb as a promoter. This catalyst is commercially available from Engelhard with the palladium present in the zero valence state, or reduced state, or may be synthesized according to the method of H. Lindlar and R. Dubuis presented in *Organic Synthesis*, Vol. 46, page 89. As received, the catalyst is effective for the selective hydrogenation of acetylene to ethylene when the feedstream $H_2/C_2H_2$ ratio is 1:1. Under these circumstances, this catalyst yields 81% conversion of acetylene to ethylene with 100% selectivity for this conversion. Catalyst activity is increased upon pre-reduction in hydrogen, yielding 100% acetylene conversion with only a slight decline in selectivity, to about 95%.

However, when the feedstream contains excess hydrogen, i.e. a 2:1 ratio of $H_2/C_2H_2$, this catalyst virtually completely converts the acetylene to ethane, maintaining 100% acetylene conversion but only yielding 0.02% selectivity to ethylene.

This catalyst's lack of olefin selectivity in the presence of excess hydrogen was corrected by the subject inventive catalyst treatment method, which involves pretreatment of the catalyst with a procedure of oxidation/reduction/thermolysis steps. This pretreatment process imparts to the catalyst increased selectivity without a correlative loss in conversion. The catalyst, pretreated according to the method disclosed herein, yields 100% conversion with selectivities of 95% or better. It is noted that selectivity may be somewhat lower initially with the pretreated catalyst, however selectivity rapidly increases with time on stream.

The inventive procedure involves four steps. First, the catalyst is oxidized by heating in air or another oxygen-containing gas stream to a temperature of between about 100°–500° C., preferably between about 200°–350° C., most preferably about 300° C., and calcining for at least about 30 minutes. The catalyst then undergoes two reduction steps, being first reduced in the presence of carbon monoxide at a temperature of between about 100°–400° C., preferably about 200°–350° C., most preferably about 300° C., for at least about 30 minutes, and then reduced in hydrogen at a temperature of between about 100°–400° C., preferably about 200°–350° C., most preferably about 300° C., for at least about 30 minutes. Optionally, these reduction steps may be combined to one step. The fourth step, the thermolysis step, involves a heat treatment of the already oxidized and reduced catalyst in the presence of an inert gas, such as nitrogen, helium, or argon, at a temperature of about 250°–600° C., preferably 300°–400° C., most preferably about 350° C. for at least about 30 minutes, and a subsequent cooling of the thermolyzed catalyst to the reaction temperature, between about 25°–350° C., in an inert gas stream. The catalyst is purged in nitrogen gas for about 5 minutes in between each step of the pretreatment process. The catalyst can be treated according to this method in situ, or it may be treated and maintained under inert conditions for future use. Further, the catalyst may be treated with only on complete cycle of the four-step process or, more preferably, may undergo the total procedure two or more times.

The selectivities reported below for hydrogenation reactions are calculated as defined by the expression:

$$100 \times [C_2H_4]/([C_2H_4]+[C_2H_6])$$

The numbers resulting from the calculation are a percentage corresponding to the ratio of the moles of "half" hydrogenated product (olefin) relative to the total moles of hydrogenation product (olefin + paraffin). Other minor reaction products include butenes and butane. Although the selectivities reported are based solely on $C_2$ products, they are also an excellent representation of total olefins produced to olefins plus alkanes produced.

Figure 2:
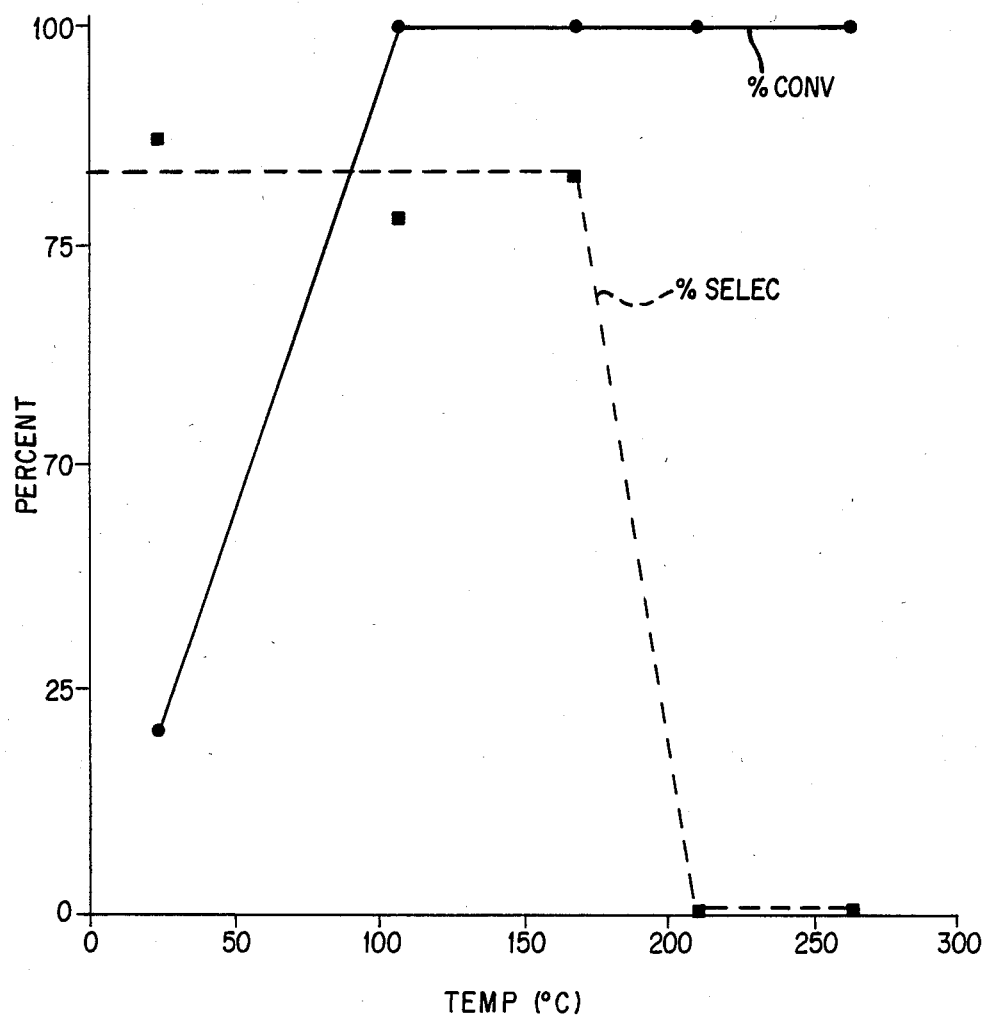
FIG. 2 is a plot of conversion and selectivity for the treated catalyst relative to temperature.

The temperature at which the hydrogenation is run is an important factor in determining the selectivity of the catalyst. FIGS. 1 and 2 demonstrate the effect of temperature upon conversion and selectivity of a given catalyst. The feed gas mixture used in generating the data represented in FIGS. 1 and 2 was synthetic PEG without excess hydrogen, the content of which was 3.41% acetylene, 2.97% ethylene, 0.5% ethane, and 2.89% hydrogen, the remainder being methane.

An untreated catalyst exhibits poor conversion at room temperature. However, when the temperature is raised to 100° C. conversion is increased to 100% and selectivity is about 77%. FIG. 1 shows conversion and selectivity for this reaction over a temperature range of 25°–350° C.

When excess hydrogen is added to the synthetic PEG, the resultant mixture being 25.9% hydrogen, 2.6% acetylene, 2.3% ethylene and 0.4% ethane, with the balance methane, which more nearly approximates an actual PEG, complete conversion of acetylene and ethylene to ethane occurs with the untreated catalyst, even at room temperature. Treating the catalyst according to the inventive method disclosed herein, however, results in greater than 95% conversion, which is slightly less than that reported for the untreated catalyst, but selectivities of between about 75–85% are attainable. FIG. 2 shows the selectivity and conversion performance of the treated catalyst used with the above excess hydrogen-containing PEG feedstream relative to temperature. A window wherein good selectivity and conversion are attainable, even in initial operation, is seen between 100° and 200° C. At temperatures lower than this the conversion rate is less, and at higher temperatures selectivity is lost. As was previously stated, time on stream is also a factor to be considered in using the catalyst. While initial selectivity is relatively low at temperatures above 200° C., the selectivity will improve with longer time on stream.

The following tables, Tables I and II, present data which relates the performance of an untreated catalyst and the treated catalyst in a feedstream containing ethylene and excess hydrogen. Table I presents reaction conditions and feedstream content for two conversion runs with an untreated catalyst (runs 1 and 2) and for two conversion runs with the treated catalyst (runs 3 and 4). Table II presents conversion and selectivity data, as well as product data, for the same four runs. These data, while not specific to the following Examples, are representative of the results obtained therein, demonstrating greatly increased selectivity of the treated catalyst over the untreated catalyst for acetylene conversion when used in the presence of ethylene and excess hydrogen.

TABLE II

CONVERSION AND SELECTIVITY FOR ACETYLENE TO ETHYLENE CONVERSION OVER Pd—Pb/CaCO$_3$

| CONVERSION RUN | CATALYST Pd—Pb/CaCO$_3$ | % $C_2H_2$ CONV. | $C_2H_4$ SEL.* | EFFLUENT $C^2$ CONTENT $C_2H_4$ | $C_2H_6$ | $C_2H_5$ |
|---|---|---|---|---|---|---|
| 1 | untreated | 99.8 | 0 | 0 | 5.41 | 0.01 |
| 2 | untreated | 99.8 | 0 | 0.07 | 5.29 | 0.01 |
| 3 | treated | 98.5 | 83 | 4.24 | 0.78 | 0.04 |
| 4 | treated | 97.4 | 89 | 6.73 | 0.98 | 0.08 |

$$*C_2H_4 \text{ SEL} = \frac{\text{moles } C_2H_4 \text{ produced}}{\text{moles } C_2H_4 + \text{moles } C_2H_6 \text{ produced}}$$

The catalyst used to generate this data experienced no irreversible changes. This was established when the same catalyst used at temperatures above 200° C. was run at 170° C. The generated data showed no loss in either selectivity or conversion.

EXAMPLES

Example 1

A mixture of 2:1 volume/volume ratio totaling 50 cm$^3$/min of hydrogen-acetylene feed was passed over 0.1 g of the Pd-Pb/CaCO$_3$ catalyst at 25° C. in a quartz tube fixed bed reactor. The reaction exotherm raised the catalyst temperature to approximately 70° C. Complete hydrogenation to ethane occurred, with 100% conversion of acetylene and only 0.02% selectivity to ethylene.

The catalyst was then pretreated according to the inventive method disclosed above. The procedure consisted of heating the catalyst to 300° C. in air and calcining for 30 minutes, followed by 30 minutes of CO and H$_2$ reductions. Finally, the reduced catalyst was heated to 350° C. under N$_2$ for 30 minutes and allowed to cool under flowing nitrogen. The 2:1 gas mixture was then passed over the pretreated catalyst under the same conditions as were used for the untreated sample. The treated sample exhibited 95% selectivity for the production of ethylene from acetylene, with 99% total conversion of acetylene.

Example 2

The hydrogen rich feed PEG of 25.9% H$_2$, 2.6% C$_2$H$_2$, 2.3% C$_2$H$_4$, 0.4% C$_2$H$_6$, the balance being methane, at 105 cm$^3$/min total feed rate, was passed over an untreated Pd-Pb/CaCO$_3$ catalyst at temperatures between 25° and 200° C. in a quartz tube fixed bed reactor. Complete conversion of acetylene and ethylene to ethane occurred.

The catalyst was then pretreated as previously described in Example 1 above. Selectivities to ethylene of 75–85% were attained with greater than 95% conversion of acetylene. Good selectivity and conversion were maintained between about 100° and 200° C. At lower temperatures conversion was somewhat less and at

TABLE 1

OPERATING PARAMETERS FOR ACETYLENE TO ETHYLENE CONVERSION OVER Pd—Pb/CaCO3

| CONVERSION RUN | CATALYST Pd—Pb/CaCO$_3$ | TEMP (°C.) | FLOWRATE CC/MIN. | CONTACT TIME (mSEC) | FEED CONTENT H$_2$/C$_2$ | C$_2$H$_4$ | C$_2$H$_6$ | C$_2$H$_2$ |
|---|---|---|---|---|---|---|---|---|
| 1 | untreated | 170 | 105.5 | 83 | 5.7 | 2.38 | 0.40 | 2.49 |
| 2 | untreated | 24 | 105.5 | 124 | 4.7 | 2.46 | 0.43 | 2.82 |
| 3 | treated | 168 | 105.5 | 83 | 5.3 | 2.27 | 0.38 | 2.64 |
| 4 | treated | 168 | 92.1 | 96 | 2.2 | 3.14 | 0.53 | 3.14 | temperatures above 200° C. selectivity decreased significantly.

The ethylene produced using the catalyst herein disclosed as treated according to the subject inventive method can then be upgraded to gasoline range hydrocarbons. The use of acidic molecular sieves to accomplish this is well known in the art. The conversion catalyst used for converting ethylene to gasoline range hydrocarbons may be any of a number of catalysts known in the art to be useful for such conversions. Exemplary catalysts include zeolite catalysts and other molecular sieving catalysts. The catalyst system employed may be either a singular catalyst or a combination of compatible catalysts.

Zeolite catalysts useful for this process include alumino silicate zeolites, preferably zeolites with ZSM-5 type structures. Molecular sieving zeolites or highly siliceous molecular sieves may also be used. They may be employed in the simple acidic form of the zeolite, or the catalyst structure may be modified with various elements, such as Ga, B, P, Al or Zn, by impregnation, ion exchange, or other known modification methods. Using a gallium impregnated ZSM-5 molecular sieving catalyst, the ethylene was converted to 62wt % $C_5+$ aromatic rich products. The liquid yield is temperature dependent. Although 100% conversion of ethylene to gasoline range hydrocarbons is achieved between 300°-500° C., selectivity changes considerably over this range, i.e., at 350° C., 22% liquids and a gaseous product rich in propane and butane form, whereas at 470° C., 62% liquids form, ethane and methane dominating the gaseous phase products.

Example 3

The combination of hydrogenating acetylene to ethylene over the pretreated catalyst, and upgrading the ethylene produced to $C_5+$ liquid products was tested. This process was accomplished in a one pass, continuous process introducing acetylene and recovering gasoline range hydrocarbons. Gases were controlled to the reactor through electronic mass flow controllers. Liquid products were collected in a U-tube at 0° C. throughout the run, and were weighed and analyzed by gas chromatography. The gaseous products were sampled by gas chromatography, and the total effluent volume was recorded on a wet test meter.

The relative weights of hydrogenation catalyst and zeolite catalyst were chosen based on data acquired for yield versus flow rate (space velocity) for each reaction. The reaction conditions were as follows: 50 cc/min of 2:1 $H_2/C_2H_2$-containing feedstream was passed over 0.1 g of $Pd-Pb/CaCO_3$ catalyst at 63° C., with the product effluent gas fed directly over 1.0 g of zeolite catalyst, at 479° C. The zeolite catalyst used was 67% of 0.5 wt. % gallium-impregnated ZSM5 and 33% $Al_2O_3$ binder.

The combined process gave 50% (wt) liquid yields per pass with 99.5% acetylene conversion. The hydrogenation step was effective at converting acetylene to ethylene. No coking or fouling, beyond the amount normal for $C_2H_4$ feed gas, was observed on the zeolite catalyst.

Example 4

A mixture of 2:1:1 $H_2:C_2H_2:C_2H_4$ at 143 cc/min was passed over the combination catalyst system as in Example 3. The pass was run at 470° C. for about one hour. The overall conversion of acetylene and ethylene in the combined process was 99.9% with a resulting yield of 68.8% $C_5+$ aromatic-rich liquid products.

This total process may be run over the acetylene hydrogenation catalyst and then separately over the catalyst for the conversion of ethylene to gasoline range hydrocarbons, or the catalysts may be combined.

Examples 1-4 demonstrate increased selectivity of an acetylene hydrogenation catalyst upon pretreatment of the catalyst according to the method disclosed herein, and use of the treated catalyst in conjunction with a suitable catalyst or catalyst system for the conversion of an acetylene-, ethylene-and hydrogen-containing feedstream to gasoline range hydrocarbons.

The scope of this invention is intended to include modifications and variations commensurate with the scope of the appended claims. The parameters herein presented, such as catalyst pretreatment conditions, and temperatures above and below which conversion and selectivity changes occur, are not intended to be limitative of this invention.

We claim:

1. A pretreatment method for imparting increased selectivity to $Pd-Pb/CaCO_3$ acetylene hydrogenation catalysts comprising at least one cycle comprising the steps of:
   (a) oxidizing said catalyst;
   (b) reducing said catalyst in the presence of carbon monoxide;
   (c) reducing said catalyst in the presence of hydrogen; and
   (d) thermolyzing said reduced catalyst,
wherein said catalyst is purged under a flow of inert gas between each step.

2. The method of claim 1 wherein step (a) takes place in an oxygen-containing gas stream.

3. The method of claim 2 wherein step (a) takes place in air.

4. The method of claim 1 wherein step (a) is performed at a temperature between about 100° and about 500° C.

5. The method of claim 4 wherein step (a) is performed at a temperature between about 200° and about 350° C.

6. The method of claim 5 wherein step (a) is performed at a temperature of about 300° C.

7. The method of claim 1 wherein step (b) is performed at a temperature between about 100° and about 400° C.

8. The method of claim 7 wherein step (b) is performed at a temperature between about 200° and about 350° C.

9. The method of claim 8 wherein step (b) is performed at a temperature of about 300° C.

10. The method of claim 1 wherein step (c) is performed at a temperature between about 100° and about 400° C.

11. The method of claim 10 wherein step (c) is performed at a temperature between about 200° and about 350° C.

12. The method of claim 11 wherein step (c) is performed at a temperature of about 300° C.

13. The method of claim 1 wherein step (d) is performed at a temperature of between about 250° and about 600° C.

14. The method of claim 13 wherein step (d) is performed at a temperature of between about 300° and about 400° C.

15. The method of claim 14 wherein step (d) is performed at about 350° C.

16. The method of claim 1 wherein step (d) is carried out in an inert atmosphere.

17. The method of claim 16 wherein step (d) is carried out in nitrogen.

18. The method of claim 1 wherein the order of step (b) and step (c) is reversed.

19. The method of claim 1 wherein said purge is carried out in nitrogen gas.

20. The method of claim 1 wherein said catalyst is cooled to the reaction temperature after step (d).

21. The method of claim 20 wherein said cooling is done in an inert atmosphere.

22. The method of claim 1 wherein said method is done in two or more cycles.

23. A method for the selective conversion of an acetylene-, ethylene-, and hydrogen-containing feedstream to gasoline range hydrocarbons comprising the steps of:
 (a) converting the acetylene in said feedstream to ethylene by passing said feedstream first over a pretreated Pd-Pb/$CaCO_3$ hydrogenation catalyst; and
 (b) passing the ethylene-containing product gas of step (a) above over a catalyst system suitable for the conversion of ethylene to gasoline range hydrocarbons,
the pretreatment of said Pd-Pb/$CaCO_3$ catalyst consisting of:
 (a) oxidizing said catalyst;
 (b) reducing said catalyst in the presence of carbon monoxide;
 (c) reducing said catalyst in the presence of hydrogen; and
 (d) thermolyzing said reduced catalyst,
wherein said catalyst is purged under a flow of inert gas between each step.

24. The method of claim 23 wherein said catalyst system is a zeolite catalyst.

25. The method of claim 23 wherein said catalyst system is a molecular sieve-containing catalyst system.

26. A pretreatment method for imparting increased selectivity to Pd-Pb/$CaCO_3$ acetylene hydrogenation catalysts comprising at least one cycle comprising the steps of:
 (a) oxidizing said catalyst;
 (b) reducing said catalyst in the presence of carbon monoxide and hydrogen; and
 (c) thermolyzing said reduced catalyst,
wherein said catalyst is purged under a flow of inert gas between each step.

27. The method of claim 26 wherein step (a) takes place in an oxygen-containing gas stream.

28. The method of claim 27 wherein step (a) takes place in air.

29. The method of claim 24 wherein step (a) is performed at a temperature between about 100° and about 500° C.

30. The method of claim 29 wherein step (a) is performed at a temperature between about 200° and about 350° C.

31. The method of claim 30 wherein step (a) is performed at a temperature of about 300° C.

32. The method of claim 26 wherein step (b) is performed at a temperature between about 100° and about 400° C.

33. The method of claim 32 wherein step (b) is performed at a temperature between about 200° and about 350° C.

34. The method of claim 33 wherein step (b) is performed at a temperature of about 300° C.

35. The method of claim 26 wherein step (c) is performed at a temperature of between about 250° and about 600° C.

36. The method of claim 35 wherein step (c) is performed at a temperature of between about 300° and about 400° C.

37. The method of claim 36 wherein step (c) is performed at about 350° C.

38. The method of claim 26 wherein step (c) is carried out in an inert atmosphere.

39. The method of claim 38 wherein step (c) is carried out in nitrogen.

40. The method of claim 26 wherein said purge is carried out in nitrogen gas.

41. The method of claim 26 wherein said catalyst is cooled to reaction temperature after step (c).

42. The method of claim 41 wherein said cooling is done in an inert atmosphere.

43. The method of claim 26 wherein said method is done in two or more cycles.

44. A single pass, continuous process for the selective conversion of an acetylene-, ethylene-, and hydrogen-containing feedstream to gasoline range hydrocarbons comprising charging said feedstream to a reactor containing a Pd-Pb/$CaCO_3$ acetylene hydrogenation catalyst and a catalyst system suitable for the conversion of ethylene to gasoline range hydrocarbons in sequence, such that said feedstream passes over said Pd-Pb/$CaCO_3$ catalyst in order to convert said feedstream to ethylene, and then said ethylene thus produced passes immediately over said catalyst system suitable for the conversion of ethylene to gasoline range hydrocarbons, said Pd-Pb/$CaCO_3$ catalyst having been first pretreated by a process consisting of:
 (a) oxidizing said catalyst;
 (b) reducing said catalyst in the presence of carbon monoxide;
 (c) reducing said catalyst in the presence of hydrogen; and
 (d) thermolyzing said reduced catalyst,
wherein said catalyst is purged under a flow of inert gas between each step.

45. A single pass, continuous process for the selective conversion of an acetylene-, ethylene-, and hydrogen-containing feedstream to gasoline range hydrocarbons comprising charging said feedstream to a reactor containing a catalyst consisting essentially of a pretreated Pd-Pb/$CaCO_3$ acetylene hydrogenation catalyst combined with a catalyst system suitable for the conversion of ethylene to gasoline range hydrocarbons, the pretreatment of said Pd-Pb/$CaCO_3$ catalyst consisting of:
 (a) oxidizing said catalyst;
 (b) reducing said catalyst in the presence of carbon monoxide;
 (c) reducing said catalyst in the presence of hydrogen; and
 (d) thermolyzing said reduced catalyst,
wherein said catalyst is purged under a flow of inert gas between each step.

* * * * *